US007113624B2

(12) United States Patent
Curry

(10) Patent No.: US 7,113,624 B2
(45) Date of Patent: Sep. 26, 2006

(54) IMAGING APPARATUS AND METHOD EMPLOYING A LARGE LINEAR APERTURE

(75) Inventor: Douglas N. Curry, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 595 days.

(21) Appl. No.: 10/271,347

(22) Filed: Oct. 15, 2002

(65) Prior Publication Data

US 2004/0071330 A1  Apr. 15, 2004

(51) Int. Cl.
*G06K 9/00* (2006.01)
(52) U.S. Cl. ........................ 382/132; 382/128; 382/140
(58) Field of Classification Search ........ 382/128–134; 600/160, 178, 181, 182, 476, 478; 356/3.02, 356/3.04, 3.06, 3.07, 139.01, 139.03, 73, 356/73.1, 460, 465, 477, 901, 139.3, 139.1; 378/98.8, 98.3, 98.4, 98.6, 98.9; 250/368
See application file for complete search history.

(56) References Cited

U.S. PATENT DOCUMENTS

| 4,002,829 | A | | 1/1977 | Hutchison |
| 4,010,364 | A | | 3/1977 | Fuwa |
| 4,556,903 | A | | 12/1985 | Blitchington et al. |
| 4,600,951 | A | | 7/1986 | Blitchington ............... 358/481 |
| 4,721,851 | A | | 1/1988 | Kogure |
| 4,849,645 | A | | 7/1989 | Mendenko et al. .... 250/559.18 |
| 4,875,780 | A | | 10/1989 | Moran et al. ............... 356/446 |
| 4,941,309 | A | | 7/1990 | Fluent et al. ............... 53/544 |
| 5,017,798 | A | | 5/1991 | Murakami et al. ...... 250/559.06 |
| 5,216,485 | A | | 6/1993 | Bird et al. .................. 356/394 |
| 5,220,617 | A | | 6/1993 | Bird et al. |
| 5,315,993 | A | * | 5/1994 | Alcala ........................ 600/341 |
| 5,471,066 | A | | 11/1995 | Hagiwara ............... 250/559.48 |
| 5,627,365 | A | * | 5/1997 | Chiba et al. ................. 250/234 |
| 5,640,246 | A | | 6/1997 | Castonguay ................. 356/445 |
| 5,651,047 | A | * | 7/1997 | Moorman et al. ......... 378/98.8 |
| 5,732,162 | A | | 3/1998 | Curry |
| 5,798,831 | A | | 8/1998 | Hagiwara ................. 356/237.2 |
| 5,892,577 | A | * | 4/1999 | Gordon ....................... 356/73 |
| 6,445,451 | B1 | * | 9/2002 | Douglas-Hamilton et al. ............................ 356/425 |
| 6,545,334 | B1 | | 4/2003 | Verhaegen |

(Continued)

FOREIGN PATENT DOCUMENTS

GB  1 579 188  11/1980

(Continued)

OTHER PUBLICATIONS

EP 03 25 6441, European Search Report, Jan. 20, 2004.

(Continued)

*Primary Examiner*—Jingge Wu
*Assistant Examiner*—Abolfazl Tabatabai
(74) *Attorney, Agent, or Firm*—Fay, Sharpe, Fagan, Minnich & McKee, LLP

(57) ABSTRACT

An apparatus images a surface. An imager stage linearly translates the surface in a first direction. A fiber optic bundle has a first end of parallel first fiber ends defining a linear input aperture perpendicular to the first direction and parallel to the surface, and a second end defining a generally circular output aperture. Each first fiber end optically communicates with the output aperture. A radiation beam linearly scans and interacts with the surface below the input aperture to produce a light signal that is collected by the input aperture and transmitted by the fiber bundle to the output aperture. A photodetector detects the light signal at the output aperture. A processor processes the detected light.

34 Claims, 7 Drawing Sheets

U.S. PATENT DOCUMENTS

| | | | |
|---|---|---|---|
| 6,582,363 B1 * | 6/2003 | Adachi et al. | 600/178 |
| 6,636,623 B1 * | 10/2003 | Nelson et al. | 382/133 |
| 2001/0046712 A1 | 11/2001 | Hang et al. | |
| 2002/0177885 A1 | 11/2002 | Eisfeld et al. | |
| 2002/0186368 A1 | 12/2002 | Rosengaus et al. | 350/237.2 |
| 2004/0071332 A1 | 4/2004 | Bruce et al. | |

FOREIGN PATENT DOCUMENTS

| | | |
|---|---|---|
| JP | 4296642 | 10/1992 |
| JP | 6148085 | 5/1994 |
| JP | 9145631 | 6/1994 |

OTHER PUBLICATIONS

Bianchi, Diana W., et al., Fetomaternal Cellular and Plasma DNA Trafficking, The Yin and the Yang, *Annals New York Academy of Sciences*, pp. 119-131.

Wolfe, Josh, A Thousand Dots of Light, *Forbes/Wolfe Nanotech Report*, May 29, 2002, www.Forbes.com.

Pertl, Barbara, MD, et al., Fetal DNA in Maternal Plasma: Emerging Clinical Applications, *The American College of Obstetricians and Gynecologists*, Published by Elsevier Science Inc., vol. 98, No. 3, Sep. 2001, pp. 483-490.

Bauer, Kenneth D., et al., Reliable and Sensitive Analysis of Occult Bone Marrow Metastases Using Automated Cellular Imaging, *Clinical Cancer Research*, vol. 6, pp. 3552-3559, Sep. 2000.

Witzig, Thomas E., et al., Detection of Circulating Cytokeratin-positive Cells in the Blood of Breast Cancer Patients Using Immunomagnetic Enrichment and Digital Microscopy, *Clinical Cancer Research*, vol. 8, 1085-1091, May 2002.

Ghossein, R.A., et al., Molecular Detection and Characterisation of Circulating Tumour Cells and Micrometastases in Solid Tumours, *European Journal of Cancer* 36 (2000) 1681-1694, Mar. 2000, Elsevier Science Ltd.

Flatmark, Kjersti, et al., Immunomagnetic Detection of Micrometastatic Cells in Bone Marrow of Colorectal Cancer Patients, *Clinical Cancer Research*, vol. 8, 444-449, Feb. 2002.

Méhes, Gábor, et al., Quantitative Analysis of Disseminated Tumor Cells in the Bone Marrow by Automated Fluorescence Image Analysis, *Cytometry (Communications in Clinical Cytometry)*, 42:357-362 (2000, Wiley-Liss Inc.

Werther, M., et al., The Use of the CELLection Kit in the Isolation of Carcinoma Cells from Mononuclear Cell Suspensions, *Journal of Immunological Methods*, 238 (2000) 133-141, 2000 Elsevier Science B.V.

Burchill, SA, et al., Comparison of the RNA-Amplification Based Methods RT-PCR and NASBA for the Detection of Circulating Tumour Cells, *2002Cancer Research Campaign, British Journal of Cancer* (2002) 86, 102-109.

Diana W. Bianchi and Y.M. Dennis Lo, "Fetomaternal Cellular and Plasma DNA Trafficking, The Yin and the Yang"; *Annals New York Academy of Sciences*; vol (Iss) 945; Sep. 2001; pp. 119-131.

Barbara Pertl, MD and Diana W. Bianchi, MD, "Fetal DNA in Maternal Plasma: Emerging Clinical Applications"; *Tthe American College of Obstetricians and Gynecologists*, Published by Elsevier Science Inc.; vol. 98, No. 3, Sep. 2001; pp. 483-490.

European Search Report, dated Apr. 5, 2006; EPC Application No. 05112479.0-2204; Examiner O. Brison, Berlin.

European Search Report, dated Jun. 2, 2006; EPC Application No. 05112370.1-2204; Examiner D. D'Alessandro.

* cited by examiner

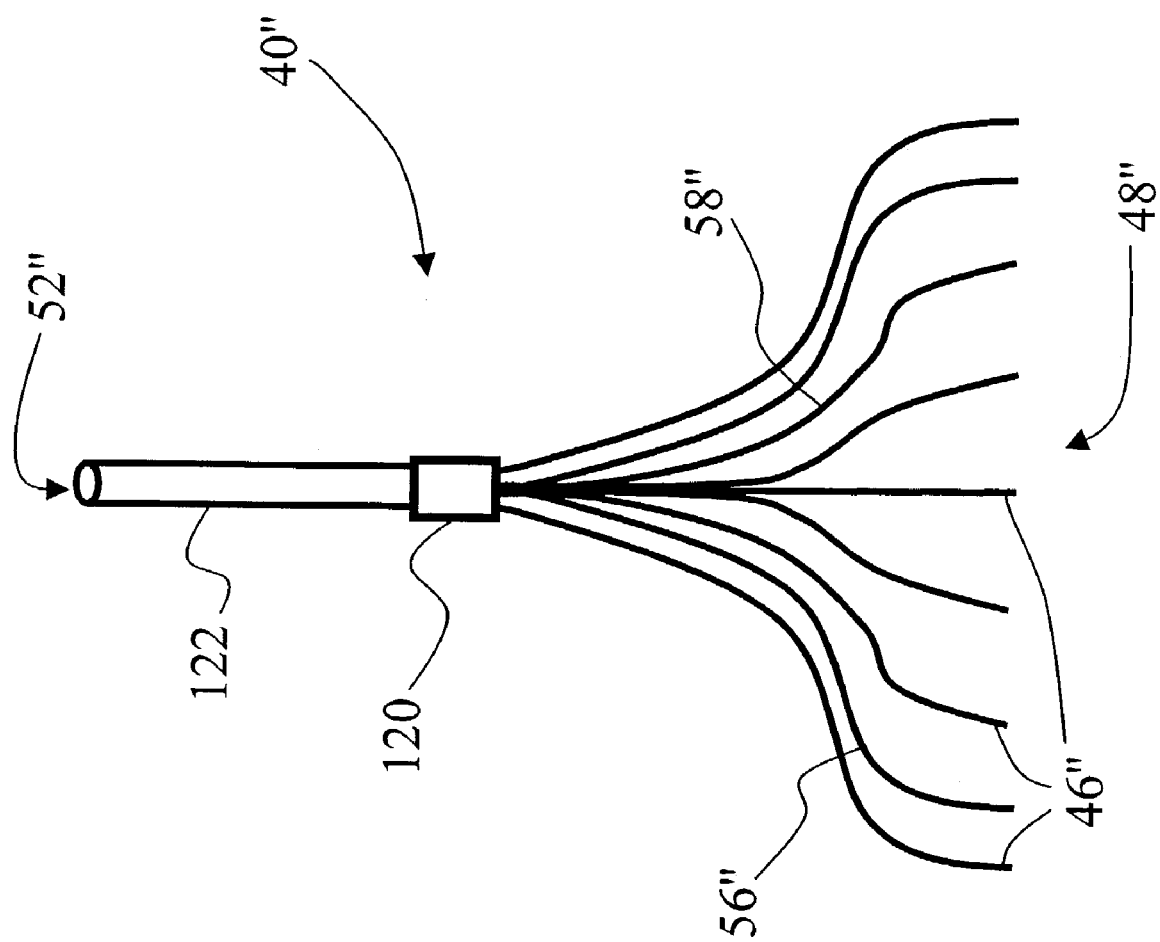

IMAGING APPARATUS AND METHOD EMPLOYING A LARGE LINEAR APERTURE

BACKGROUND OF THE INVENTION

The present invention relates to the imaging arts. It finds particular application in conjunction with low and high-density cell detection in blood smears, biological assays, and the like, and will be described with particular reference thereto. However, it is to be appreciated that the present invention will also find application in imaging other types of low- or high-density features on various substantially planar surfaces and samples, such as imaging semiconductor wafers, imaging particulate contaminants in fluids or thin solid films, and so forth, with such imaging finding specific uses in the printing arts, electronic arts, medical arts, and other scientific and engineering areas.

With particular attention to cell detection, it has been determined by the inventors that a beneficial aspect to which the present application may be applied is to scan a large number of cells, such as 1 to 10 million cells, at a time. Thereafter, the concepts of the application may be used to identify either a small number of these cells, such as rare cells found in cancer, etc., or to be able to characterize each one of the scanned cells for use in research applications.

Clinical prenatal care benefits from directly accessing fetal tissues. In conventional amniocentesis, amniotic fluid surrounding the fetus is directly accessed and drawn. The amniotic fluid includes fetal cells which are extracted for study. To reduce risk to the fetus, ultrasound monitoring is typically performed during the amniocentesis to ensure that the probe needle does not contact or interfere with the fetus, and the amniocentesis procedure is performed by skilled clinical personnel. Nonetheless, amniocentesis is known to increase the risk of miscarriage.

As an alternative to amniocentesis, rare fetal cells in the maternal bloodstream can be extracted. It is known in the prenatal medical arts that fetal cells cross the placental barrier and enter the maternal bloodstream. The concentration of fetal cells in the maternal bloodstream is typically on the order of one fetal cell for every one million maternal cells. Such "rare" fetal cells can be extracted by drawing maternal blood or by other fluid extraction. DNA analysis, fetal blood typing, or other clinical studies are performed on the rare fetal cells to provide information about the fetus. Unlike amniocentesis, extraction of rare fetal cells from the maternal bloodstream is isolated from the fetus and the womb, and the extraction can be performed by a broad range of medical personnel authorized to draw blood.

In the clinical oncology arts, it is recognized that cancerous cells are typically present in small concentrations in a cancer patient's bloodstream. In the case of deep malignant tumors which are inaccessible except by invasive surgery, rare cancerous cells extracted from blood or another body fluid provide a convenient and cost effective pathway for detecting a cancer, periodically monitoring cancer remission, and diagnosing a cancer type. Rare cell analysis targeting cancerous cells is a promising diagnostic and monitoring technique for many types of cancers, including breast, lung, colon, and prostate cancers.

In these and other rare cell studies, a problem arises because the concentration of the rare cells in the blood or other body fluid is typically very low. In a typical rare cell study, blood is processed to remove cells that that are not needed. Then a fluorescent material is applied that attaches to antibodies, which in turn selectively attach to a cell surface or cellular protein of the rare cells. The fluorescent material may be a fluorescent marker dye or any other suitable material which will identify the cells of interest. A blood smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells for a one-in-one million rare cell concentration. Such a blood smear typically occupies an area of about 100 cm$^2$. It is to be understood, however, that this is simply one example and other numbers of cells may be required for statistical accuracy for a particular test or study.

Turning to research applications, the scanning of a large number of cells and the characterization of each of the scanned cells may also have substantial benefits. For example, a hundred different patches, each containing 10,000 cells, may be generated where each patch will receive a different protocol or process. Thereafter it may be useful to determine how each cell on a specific patch is affected by the protocol or process which it has undergone. One procedure of achieving such detection would be to apply a fluorescent material, and to identify those cells to which the material has become attached either to the cell's surface, cellular proteins or other portions of the cell.

A particular area of research which may benefit from the present concepts includes HIV research, where it is known the virus enters into a cell causing the cell to produce the viral protein on its membrane. However, the produced viral protein exists in very small amounts, and therefore it is difficult to detect affected cells with existing technology.

A problem with cell analysis is the use of conventional technology which have relatively small fields of view (FOV), such as microscopes. To overcome the FOV limitation, cell analyses often employ automated high-speed scanning which however produces substantial undesirable acceleration forces on the scanned stage.

Another problem in cell studies, for both high and low density situations, is that the fluorescence intensity produced by treated cells is low, around 1000–2000 flours (fluorescent molecules). A high numerical aperture for the light-collecting aperture is preferred in the optical analysis system to provide good light collection.

Yet another problem in the cell studies is resolution. For example, if a cell has a diameter of about ten microns, the optics for the cell analysis preferably provides a resolution of this order. However, achieving high resolution typically requires a reduced field of view and consequently results in a decreased scanning speed and increased required sampling time.

The present invention contemplates a new and improved apparatus and method which overcomes the above-referenced problems and others.

BRIEF DESCRIPTION OF THE INVENTION

In accordance with one aspect of the present invention, an imager for imaging a sample is disclosed. An imager stage supports the sample. A fiber optic bundle has a proximate bundle end of first fiber ends arranged to define an input aperture viewing the sample on the microscope stage. The fiber optic bundle further has a distal bundle end of second fiber ends arranged to define an output aperture shaped differently from the input aperture and disposed away from the imager stage. A scanning radiation source is arranged in fixed relative position to the input aperture. The scanning radiation source scans a radiation beam on the sample within a viewing area of the input aperture. The radiation beam interacts with the sample to produce a light signal that is reflected, scattered, transmitted, re-emitted, or otherwise collected and received by the input aperture and transmitted via the fiber optic bundle to the output aperture. The scanning radiation source rasters the radiation beam over a selected area of the sample. A photodetector is arranged to detect the light signal at the distal bundle end, and a processor processes the detected light signals.

In accordance with another aspect of the present invention, an imager for imaging a generally planar surface is disclosed. A linearly translating stage linearly translates the surface in a first direction. A fiber optic bundle has a first end of parallel first fiber ends arranged to define a linear input aperture disposed perpendicular to the first direction and parallel to the surface. The fiber optic bundle further has a second end defining a generally circular output aperture. Each first fiber end optically communicates with the generally circular output aperture. A scanning radiation source linearly scans a radiation beam along the generally planar surface below the input aperture. The radiation beam interacts with the surface to produce a light signal that is collected by the input aperture and transmitted by the fiber optic bundle to the output aperture. A photodetector is arranged to detect the light signal at the generally circular output aperture. A rastering processor communicates with the imager stage and the scanning radiation source to coordinate the scanning of the radiation beam and the linear translation of the surface to effectuate a rastering of the radiation beam on the surface.

In accordance with another aspect of the present invention, an imaging method is provided. A radiation beam is swept along a linear path on a sample. Light produced by the beam interaction with the sample is collected using at least one proximate element of an array of fiber optic ends. The collected light is transmitted along a fiber associated with the at least one proximate element. The fiber channels the collected light to a selected output region. A largest spatial dimension of the output region is substantially smaller than a largest spatial dimension of the array of fiber optic proximal ends. The collected light is detected at the selected output region. The sample is moved generally perpendicularly to the linear path of the radiation beam sweeping. The moving cooperates with the sweeping to produce a raster pattern of the radiation beam on the sample. The sweeping, moving, and detecting are coordinated to generate an array of picture elements representative of at least a portion of the sample.

In accordance with yet another aspect of the present invention, an apparatus is disclosed for identifying rare cells in a biological smear. The rare cells emit a characteristic luminescence responsive to exposure to an excitation radiation. A translating imager stage laterally translates the biological smear in a first direction. A fiber optic bundle includes a plurality of fibers each having a first end and a second end. The first ends are arranged to define a generally rectangular receiving aperture having a large aspect ratio whose long dimension is perpendicular to the first direction. The second ends are arranged to define an output aperture having a compact shape. A radiation source linearly sweeps an excitation radiation beam across the biological smear with a sweep direction perpendicular to the first direction. An interaction region of the radiation source and the biological smear is arranged relative to the receiving aperture such that characteristic luminescence produced in the interaction region is collected by the receiving aperture. A photodetector is arranged to detect the collected characteristic luminescence at the output aperture. A controller controls the translation of the imager stage and the sweeping of the radiation source to raster the excitation radiation beam across the biological smear to identify rare cells in the biological smear based upon the characteristic luminescence detected during the rastering.

In accordance with still yet another aspect of the present invention, an imaging apparatus is disclosed for imaging a sample. An imager stage supports a slide on which the sample is disposed. The slide includes a wavelength-selective filter disposed thereon which substantially blocks light at an excitation light wavelength. A radiation source includes a light source that emits excitation light at the excitation light wavelength, and optics that convert the emitted excitation light into converging excitation light that impinges as a spot of suitable resolution on the sample. Interaction between the excitation light and the sample generates luminescence light at a different wavelength from the excitation light wavelength. An input aperture is arranged to collect at least a portion of the luminescence light. The input aperture is arranged on an opposite side of the slide from the impinging excitation light such that the wavelength-selective filter substantially blocks excitation light from being collected by the input aperture. An output aperture optically communicates with the input aperture and emits the luminescence light collected by the input aperture. Numerous advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 6 diagrammatically shows another fiber optic bundle embodiment that is suitable for use in the apparatus of FIGS. 1–4 or the apparatus of FIG. 5.

DETAILED DESCRIPTION OF THE INVENTION

Figure 1:
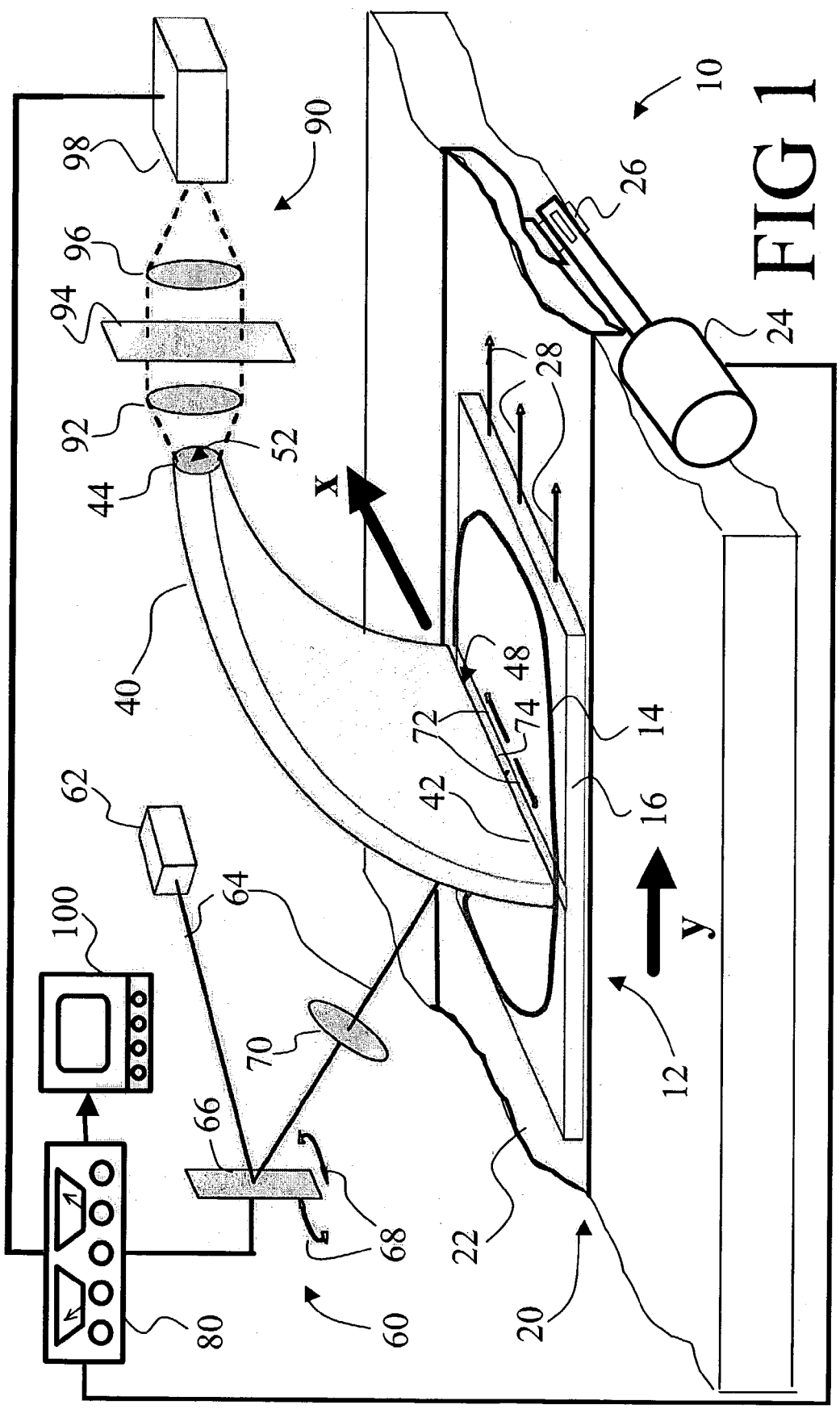
FIG. 1 shows a perspective view of an imaging apparatus formed in accordance with a preferred embodiment of the invention.

With reference to FIG. 1, an imaging apparatus or imager 10 examines a sample 12 such as a biological smear 14 disposed on at least a portion of a surface of a slide 16. Imaging apparatus or imager 10, as expanded upon below, is designed for detection of minute or microscopic material. It is to be appreciated that while the following discussion describes imager 10 in connection with specific material of certain sizes, it is not intended to be limited to use only in connection with these materials and these sizes, but rather is considered applicable to all materials and sizes, which would be detectable by the described device and method. Further, the imaging apparatus and imager are intended to include all appropriate image forming devices, including but not limited to a microscope and digital image.

As is known in the art, for cell studies the sample 12 is suitably prepared by drawing a sample of a biological fluid such as, but not limited to, blood or parts of blood from a subject. The fluid sample is treated with a fluorescent material, such as but not limited to a marker dye, that selectively bonds to a cell surface, cellular protein, or other element of the cell, optionally via an anti-body or other intermediary element. Suitable materials are known in the art for marking a number of different cell types of clinical interest, including selected cancer cell types, fetal cells, or other appropriate cells to be considered. The material preferably emits a characteristic luminescence, such as a fluorescence or a phosphorescence, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths.

The treated biological fluid is smeared onto a transparent slide using known techniques. In one suitable technique, a drop of the fluid is applied to the transparent slide 16, and an edge of a second transparent slide or other well-defined, clean edge is used to spread the drop across the slide 16. In another suitable technique, the fluid is applied while the slide 16 is being rotated by a spinner, so that centrifugal forces cause the fluid to smear out substantially uniformly over the slide 16. Other methods for preparing the biological smear can be substituted for the exemplary techniques.

The smear size will depend on the implementation, however, as an example, in one situation for a rare cell concentration of about one rare cell of interest per one million cells in the biological fluid, the smear 14 might contain at least ten million cells and occupy an area of about 100 cm². Of course, larger or smaller smears can be prepared which are suitable for the anticipated concentration of cells in the sample and the desired minimum measurable cell concentration.

The sample 12 is mounted on an imager translation stage 20 (shown in part) which includes a linearly translatable track 22 that supports the sample 12. A motor 24 connects with the track 22 via gearing 26 to translate the track 22 and the supported sample 12 along a y-direction (indicated by arrows 28). Although translation stage 20 driven by a rotary motor 24 is shown in FIG. 1, it is also contemplated to employ other types of mechanical driving devices. Furthermore, other types of sample movement such as sample rotation are also contemplated.

Figure 2:
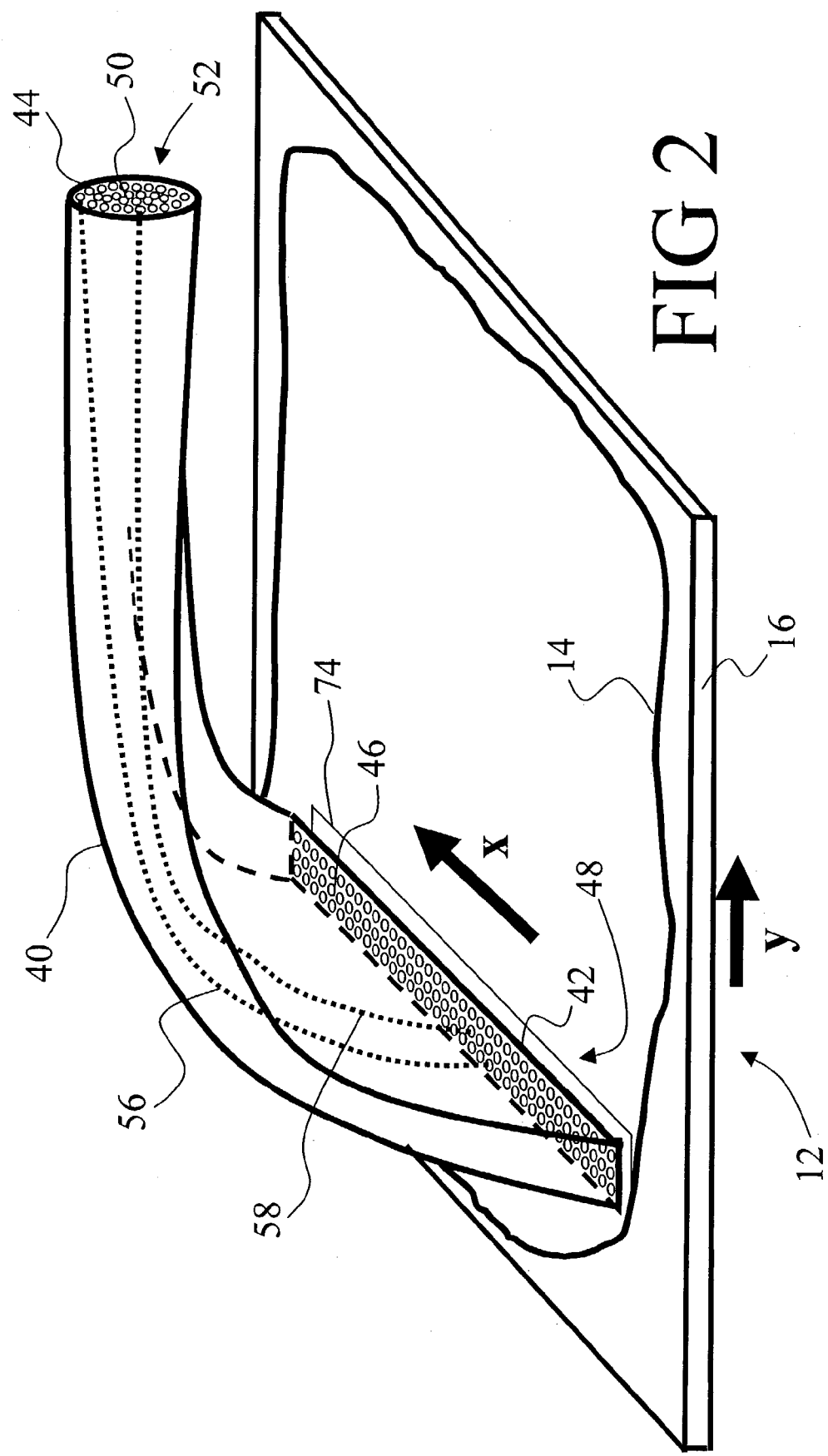
FIG. 2 shows an enlarged perspective view of the morphed fiber optic bundle of the imaging apparatus of FIG. 1 in relation to the sample.
Figure 3:
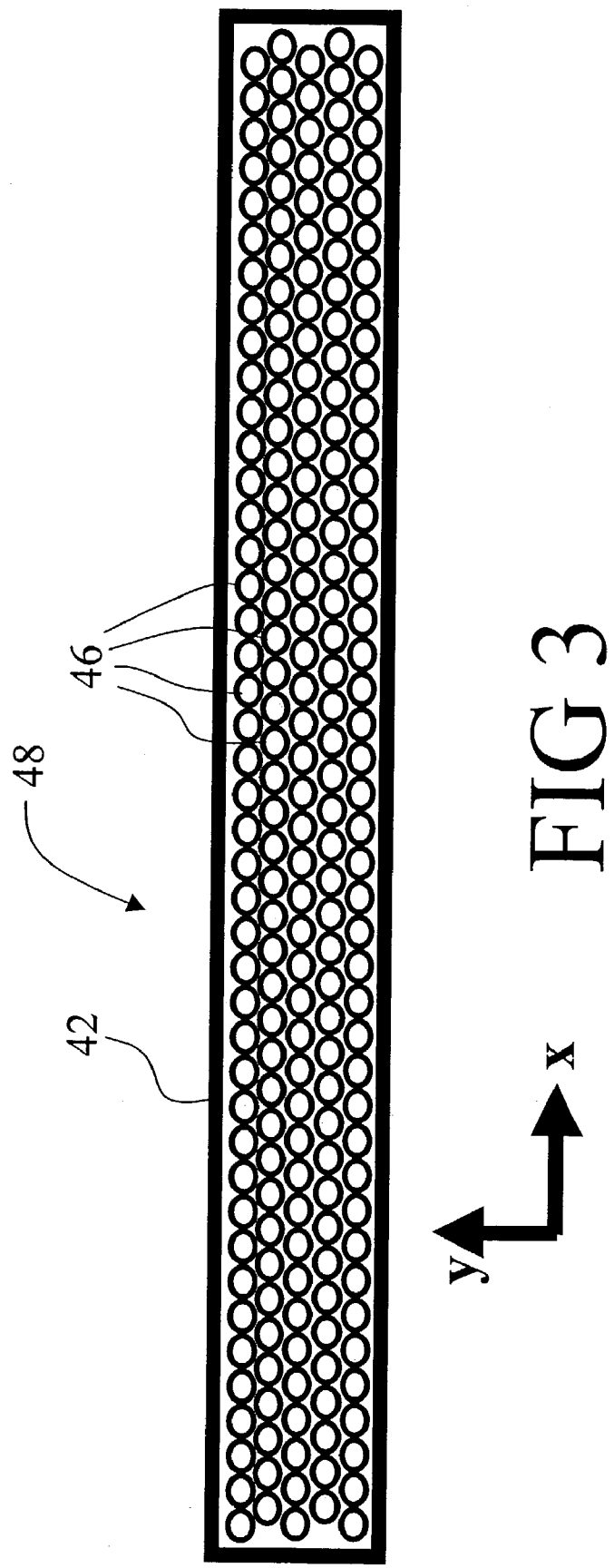
FIG. 3 shows an enlarged end view of the first end that defines the input aperture of the morphed fiber optic bundle of the apparatus of FIG. 1.

With continuing reference to FIG. 1 and with further reference to FIGS. 2 and 3, a fiber optic bundle 40 includes a first end 42 that is proximate to the sample 12, and a second end 44 that is distal from the sample 12. The first end 42 includes a plurality of first fiber ends 46 arranged substantially parallel to one another in an arrangement that defines a generally linear or high-aspect-ratio rectangular input aperture 48 (best seen schematically in FIG. 3) with a long dimension aligned with an x-direction. The input aperture 48 preferably includes a large number of first fiber ends 46, i.e. thousands of fiber ends. In one suitable embodiment, 40,000 fibers each having an approximately 50 micron diameter are arranged into a 40 fiber-by-1000 fiber array to define the input aperture 48 with a long dimension of approximately 5 cm and a short dimension of about 0.2 cm corresponding to a 25:1 aspect ratio. The first fiber ends 46 can be arranged in a regular pattern, as shown in FIG. 3. Alternatively, the first fiber ends can be arranged in an irregular or non-periodic array. Although generally round fiber ends are shown, it is also contemplated to employ fibers with oval, square, hexagonal, or other cross-sectional shapes. The first fiber ends 46 are oriented substantially perpendicular to the plane of the biological smear 14 so as to view the smear 14.

The optical fiber bundle 40 "morphs" or changes cross-sectional dimensions and shape between the first end 42 to the second end 44 such that the second end 44 includes a plurality of second fiber ends 50 (best seen schematically in FIG. 2) that define a compact, generally circular output aperture 52. Preferably, there is a one-to-one correspondence between the first fiber ends 46 and the second fiber ends 50, and each first fiber end connects with a second fiber end by an individual, distinct fiber having its own waveguiding cladding. Alternatively, each fiber can include only a light-transmissive fiber core, and an ambient/core interface functions to waveguide the light. Other optical fiber types can also be used, such fibers being well known in the art and typically formed of glass, plastic, or other light-transmissive materials by extrusion methods. In FIG. 2, the paths of two exemplary individual, distinct fibers 56, 58 are indicated as dotted lines. The morphed shape of the fiber bundle 40 from an extended, generally linear first end 42 to a compact, generally circular second end 44 is preferably formed by varying a spatial arrangement of the fibers of the optical fiber bundle 40 in a continuous fashion. For the exemplary 40,000 fiber embodiment with each fiber having a 50 micron diameter, the generally circular output aperture 52 has a circular diameter of about 1.3 cm.

It is particularly pointed out that the spatial relationship between the first fiber ends 46 and the second fiber ends 50 is generally arbitrary. For example, in FIG. 2 the fibers 56, 58 run from approximately the same position in the input aperture 48. However, the fiber 56 terminates near a top of the output aperture 52, while the fiber 58 terminates near a middle of the output aperture 52. Although for convenience in arranging the fibers it is contemplated to arrange the first and second fiber ends 46, 50 in the respective apertures 48, 52 with a selected correspondence relative to one another, the fiber ends 46, 50 can instead have a generally uncorrelated and arbitrary relationship therebetween. Morphed fiber optic bundles similar to the fiber optic bundle 40 are known and used in the optical arts for other applications such as transforming focused light into a linear illumination pattern, and for coupling a light beam into a linear slit of a monochromator or spectrometer.

To obtain good light transmission, the fiber optic bundle 40 preferably has a high fiber packing factor, for example, fiber optic bundle 40 has a packing factor of about 0.80 or higher. Other factors influencing the light transmission include the polishing or light transmission properties of the tips of the first and second fiber ends 46, 50, the absorption per unit length of the fibers 56, 58, and the overall length of the fibers 56, 58. Fiber bending losses are preferably reduced by avoiding sharp bends of the fiber optic bundle 40. For example, as seen in FIGS. 1 and 2, the difference in orientation of the input aperture 48 and the output aperture 52 is achieved by a gradual bend in the optical fiber bundle 40.

Figure 4:
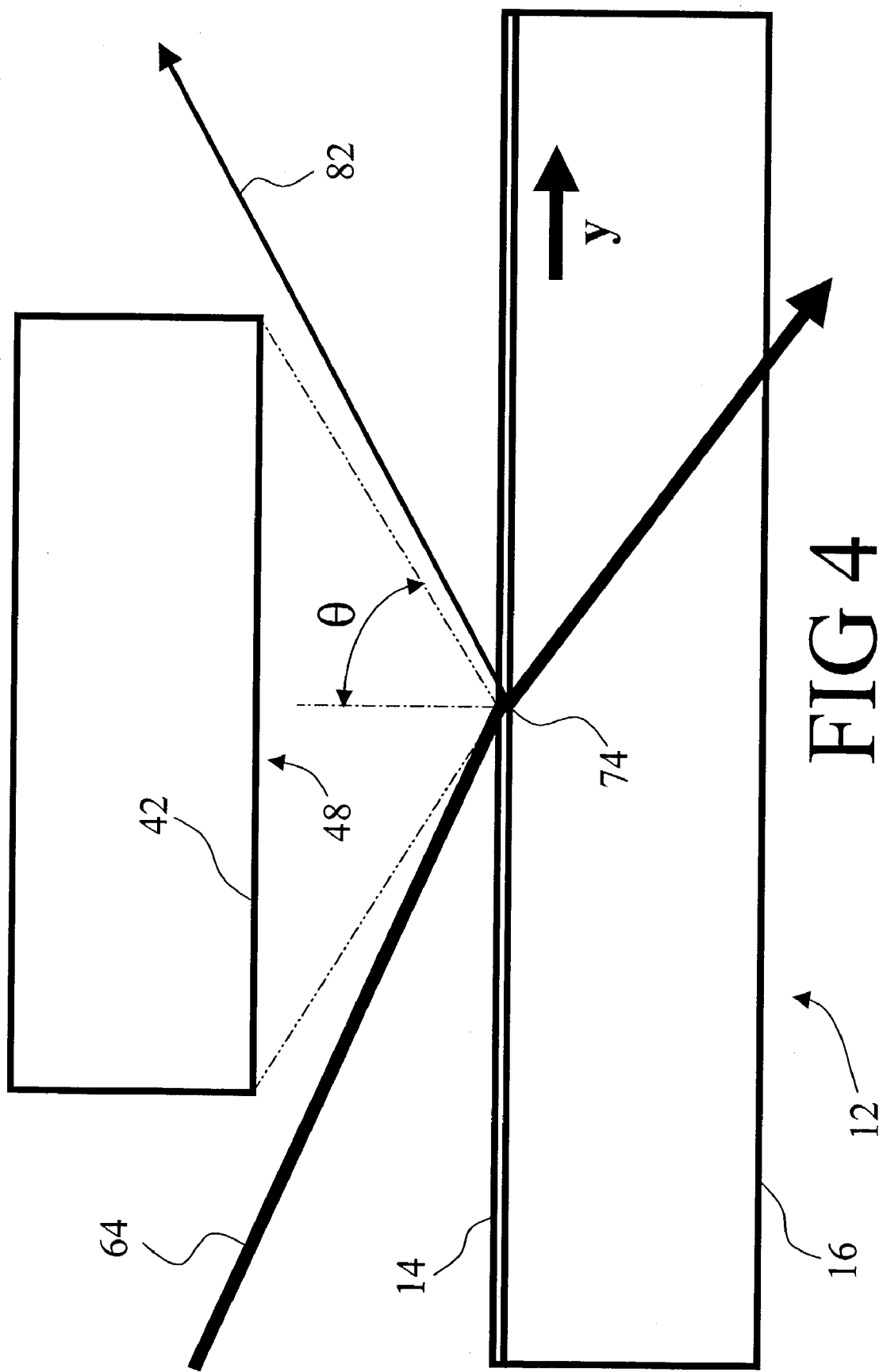
FIG. 4 shows a side view of the imaging apparatus of FIG. 1 centered on the first end of the morphed fiber optic bundle.

With continuing reference to FIGS. 1–3 and with further reference to FIG. 4, a scanning radiation (light) source 60 in a suitable embodiment includes a laser 62 that produces excitation light (radiation beam) 64 at a wavelength or wavelength range selected to excite the material used in marking the biological smear 14. The excitation light 64 is angularly scanned by a galvanometer 66 that has a reflective surface that rotates (indicated by curved arrows 68) responsive to an electrical input. An optional focusing lens 70 focuses the angularly scanned excitation light 64 onto the sample 12, and more particularly onto the biological smear 14. The angular scanning produced by the galvanometer 66 translates into a linear sweeping or scanning (indicated by arrows 72) of the excitation light on the biological smear 14 along a linear trajectory 74 arranged below the input aperture 48 and parallel to the long dimension of the input aperture 48. That is, using the coordinate system of FIG. 1 the linear trajectory 74 is parallel to the x-direction. In a suitable embodiment, the trajectory 74 is disposed on the biological smear 14 about one millimeter below the input aperture 48, although other distances will be appropriate dependant upon devices and the environment in which these concepts are implemented.

For cell studies, the excitation radiation 64 preferably produces a spot size on the biological smear 14 which substantially comports with a size of the cells, which may vary in size but are typically about one to thirty microns in size. To obtain such narrow beam focusing, the focusing lens 70 is typically included.

Those skilled in the art can make other suitable changes and substitutions in scanning radiation or light source 60 to accommodate specific applications. For example, the laser 62 can be replaced by an incandescent light source, light emitting diode (LED), or the like. The galvanometer 66 can be replaced by another optical scanning device, such as a polygon laser scanner similar to a type commonly employed in laser printers. The polygon laser scanner advantageously scans the beam more rapidly than the galvanometer 66. Furthermore, the scanning radiation or light source 60 shown in FIG. 1 can be replaced by a scanning x-ray source or a scanning electron beam employing beam deflectors. In the latter embodiment, the electron beam path is suitably enclosed in a vacuum environment.

With continuing reference to FIGS. 1–4, an electronic control unit 80 communicates with the galvanometer 66 and the translation stage 20 to coordinate the linear sweeping or scanning 72 of the radiation beam 64 along the trajectory 74 and the linear translation 28 of the sample 12 to effectuate a rastering of the radiation beam 64 across a selected area of the sample which is bounded in the x-direction by the smaller of a span of the trajectory 74 and the long dimension of the input aperture 42. Preferably, the span of the trajectory 74 substantially comports with the long dimension of the input aperture 42.

As best seen in FIG. 4, the excitation radiation beam 64 is incident upon the biological smear 14 at an oblique angle which is larger than a collection angle θ of the input aperture 42. The collection angle θ depends upon a short dimension of the input aperture 42, the distance between the input aperture 42 and the biological smear 14, and the light collecting characteristics of the first fiber ends 46. The latter is suitably characterized by a numerical aperture of the fiber ends. As is known in the art, an optical fiber end typically has a large numerical aperture corresponding to a large light collection angle which is particularly advantageous for collecting the typically weak characteristic luminescence of the cells. In a suitable embodiment, the radiation beam 64 impinges upon the sample 12 at 30°–90°, and preferably about 60° off the normal.

Because the incidence angle of the radiation beam 64 is larger than the collection angle θ of the input aperture 42, specularly reflected radiation 82 is not collected by the input aperture 42. However, the characteristic luminescence produced by the treated cells generally emits uniformly in all spatial directions, i.e. each treated cell corresponds to a point light source. Hence, a substantial portion of the characteristic luminescence is collected by the input aperture 42 due to its close proximity to and alignment with the radiation beam trajectory 74 on the biological smear 14 as well as the large numerical aperture of the first fiber ends 46. The collected light enters the first fiber ends 46, transmits along the individual fibers, e.g. the fibers 56, 58 shown in FIG. 2, and exits the optical fiber bundle 40 at second fiber ends 50 that correspond to the collecting first fiber ends 46.

It will be appreciated that the characteristic luminescence produced by a particular cell will not generally be collected by all or even most of the first fiber ends 46. Rather, only one or a few of the first fiber ends 46 which are closely proximate to the cell will collect the characteristic luminescence therefrom. In an exemplary embodiment, the radiation spot size is about 10 microns corresponding to a similarly sized cell, while each first fiber end 46 has a diameter of about 50 microns. Hence, only one or a few fibers will view and collect the characteristic luminescence for any given position of the sweeping radiation beam 64.

However, because at the second end 44 of the fiber bundle 40 the second fiber ends 50 are arranged to define the compact, output aperture 52, the characteristic luminescence emanates from a small region of space corresponding to the output aperture 52 regardless of which of the first fiber ends 46 collected the characteristic luminescence. As the excitation beam 64 sweeps along its trajectory 74 parallel to and typically below the input aperture 48, the proximate one or few of the first fiber ends 46 collect the characteristic luminescence, which is channeled by the fiber optic bundle 40 to the compact output aperture 52.

In the arrangement of FIG. 1, the scanning radiation source 60 and the input aperture 48 are arranged in fixed relative position, the galvanometer 66 provides a linear sweeping of the excitation beam 64 along the x-direction, and the sample 12 is moved by the translation stage 20 linearly along a y-direction to effectuate a two dimensional rastering. However, other rastering arrangements are also contemplated. In another suitable rastering arrangement, the input aperture has a smaller aspect ratio, i.e. a larger short dimension, such that the aperture spans the selected imaging area in both the x- and the y-directions. The scanning radiation source performs two dimensional rastering in both the x- and y-directions, while the sample remains stationary on the translation stage.

In yet another suitable rastering arrangement, the translation stage provides a rotational sample motion about a rotational axis normal to the scanned sample surface, and the input aperture has a generally linear shape, i.e. large aspect ratio, with its long dimension extending radially away from the rotational axis. The radiation beam sweeps linearly along the linear input aperture while the sample rotates to effectuate a rotational two-dimensional scanning.

In any of these rastering arrangements, the spatially distributed input aperture collects the characteristic luminescence using one or a few first fiber ends, and transmits the collected light to a compact second aperture via a morphed fiber optic bundle. As the rastering progresses, different first fiber ends perform the light collecting, but the light is continually channeled to a common compact output aperture for detection.

With reference to FIG. 1, a suitable signal detector 90 is arranged to detect the collected characteristic luminescence emanating from the output aperture 52. A first lens 92 substantially collimates the light. A light, such as but not limited to a laser light, blocking filter 94 is optionally provided to remove scattered laser light from the collected light. Although as shown in FIG. 4 the radiation beam 64 is preferably arranged so that reflected radiation 82 is not collected by the input aperture 48, typically some of the radiation beam 64 will be scattered by the sample 12 and collected by the input aperture 48. Because of the typically low intensity of the characteristic luminescence from the cells, even the collected scattered laser light can substantially interfere with signal detection.

In one suitable embodiment, the blocking filter 94 is an interference filter with a reflectance peak coinciding with a center wavelength of the radiation beam 64 is employed. As is known in the art, optical interference filters have a rejection ratio that is strongly dependent upon the angle of incidence of the light. An exemplary interference filter used in one actually constructed embodiment exhibits a $10^6$:1 or greater rejection ratio for light incident within ±14° of normal incidence. In this constructed embodiment, the first lens 92 includes a lens combination, designed using known optical design methods, that collimates light emanating from the output aperture 52 to within a ±10° angular divergence.

With continuing reference to FIG. 1, a second lens 96 focuses the collimated collected light onto a photodetector arrangement 98. By combining the compact output aperture 52 with focusing optics 92, 96, photodetector 98, which may be a single photodetector, provides signal detection for the spatially distributed linear input aperture 48. Because of the typically low collected characteristic luminescence intensities produced by treated cells, the photodetector 98 is preferably a photomultiplier tube. As is known in the art, a photomultiplier tube provides substantial signal gain through cascade multiplication of electrons in a multi-stage high-voltage cathode. To further improve the signal-to-noise ratio, the optical path of the signal detector 90 is preferably enclosed to substantially reduce noise due to stray light.

Those skilled in the art can suitably modify the signal detector 90 by addition, removal, or substitution of components to adapt it to specific imaging situations. For applications providing an alternate signal-to-noise characteristics, a photodiode can be used for the photodetector 98. Similarly, the single photodetector 98 and multiple focusing elements 92, 96 can be replaced by a photodetector array having an area that comports with an area of the output aperture 52.

In contrast, it is to be appreciated that for certain applications, such as but not limited to microscope applications, not involving luminescence, i.e., collection of reflected, transmitted or scattered radiation from the scanning spot, blocking filter 94 is optionally omitted. When blocking filter 94 is omitted and the output aperture 52 has a small enough area, the optics 92, 96 may be omitted entirely while retaining the use of a single photodetector that substantially spans the small output aperture area. Alternatively, in luminescence applications, optics 92 and 96 may also be omitted when the blocking filter 94 embodied as an interference or reflection filter, is located on the slide, when the fiber bundles themselves are made of an absorptive filter material, or the slide is the absorptive blocking filter.

In one embodiment, the blocking filter, which is an interference filter, may be an interference filter set such as developed by Chroma Technologies Corporation of Brattleboro, Vt. These filter sets are commonly used for fluorescence microscopes (a dichroic mirror long pass filter and an emitter ban pass filter) which is typically used to divert and exclude laser light from a signal path. The dichroic mirror is placed at 45° and is properly used to deflect the excitation beam (i.e., laser light) out of the path at right angles. The emitter filter is properly placed normal to the path of the excitation beam after the mirror filter and is typically used to further block the excitation beam, passing the fluorescence signal onto the detector.

In other embodiments, absorptive filters, such as Schott OG515 (from Schott Glass Technologies, Inc. of Duryea, Pa., may be added to further exclude the excitation beam (i.e., laser light). It needs to be appreciated the foregoing simply provides details to examples of filters which may be used, and this discussion is not intended to limit the disclosures to these particular filters, but rather, when the filter design is incorporated, the present application is intended to be used with any appropriate filter design.

With continuing reference to FIG. 1, the electronic control unit 80 communicates with the galvanometer 66 and the translation microscope stage 20 to raster the radiation beam 64 across the sample. Characteristic luminescence produced by interaction of the radiation beam 64 with treated cells in the biological smear 14 is collected by the input aperture 48, channeled to the output aperture 52 by the optical fiber bundle 40, and detected by the signal detector 90. The electronic control unit 80 receives the detected signal from the photodetector 98, and correlates the detected signal with positional coordinates of the radiation beam 64 on the sample 12.

In particular, the electronic control unit 80 identifies a beam sweep position as a first coordinate in the x-direction, and a position of the translation microscope stage 20 as a second orthogonal coordinate in the y-direction, to spatially map out the collected characteristic luminescence intensity as a function of position on the sample 12. The x- and y-coordinates can be inferred from the laser scan velocity and stage translation velocities, respectively. Alternately, registration marks on the sample media can be included to identify absolute x,y position information. In addition, one or both of the galvanometer 66 and the translation stage 20 can include a position sensor which is read by the electronic control unit 80 to ascertain the coordinates of the radiation beam 64 on the sample. The electronic control unit 80 suitably formats the detected signal and spatial coordinates information and stores the information in an internal memory, writes the information to a non-volatile storage medium such as a magnetic or optical disk, formats and displays an image representation including an array of picture elements with coordinates mapped to the spatial coordinates information and an intensity or color mapped to the detected signal intensity on a display 100, or the like.

Those skilled in the art can modify the electronic control unit 80 and associated devices such as the display 100 for specific applications. In a preferred embodiment, a personal computer performs the control and data collection functions of the electronic control unit 80 and includes a display and printer for displaying the image representation, and further includes a user interface for user input of a selected imaging area and other imaging setup information, a hard disk for storing the formatted detected signal and spatial coordinates information, and an optional network connection for electronically transmitting the information to other devices.

The detected signal and spatial coordinates information can be used in various ways. For monitoring a cancer remission state in a patient, a count of rare cells corresponding to the monitored cancer type in a standard smear area, e.g. a 5 cm×20 cm standard smear, can provide a useful figure of merit for the monitoring. For medical diagnostic applications, the identified rare cells are preferably extracted using known methods, and suitable DNA analysis or other diagnostic clinical testing is performed on the extracted rare cells.

Figure 5:
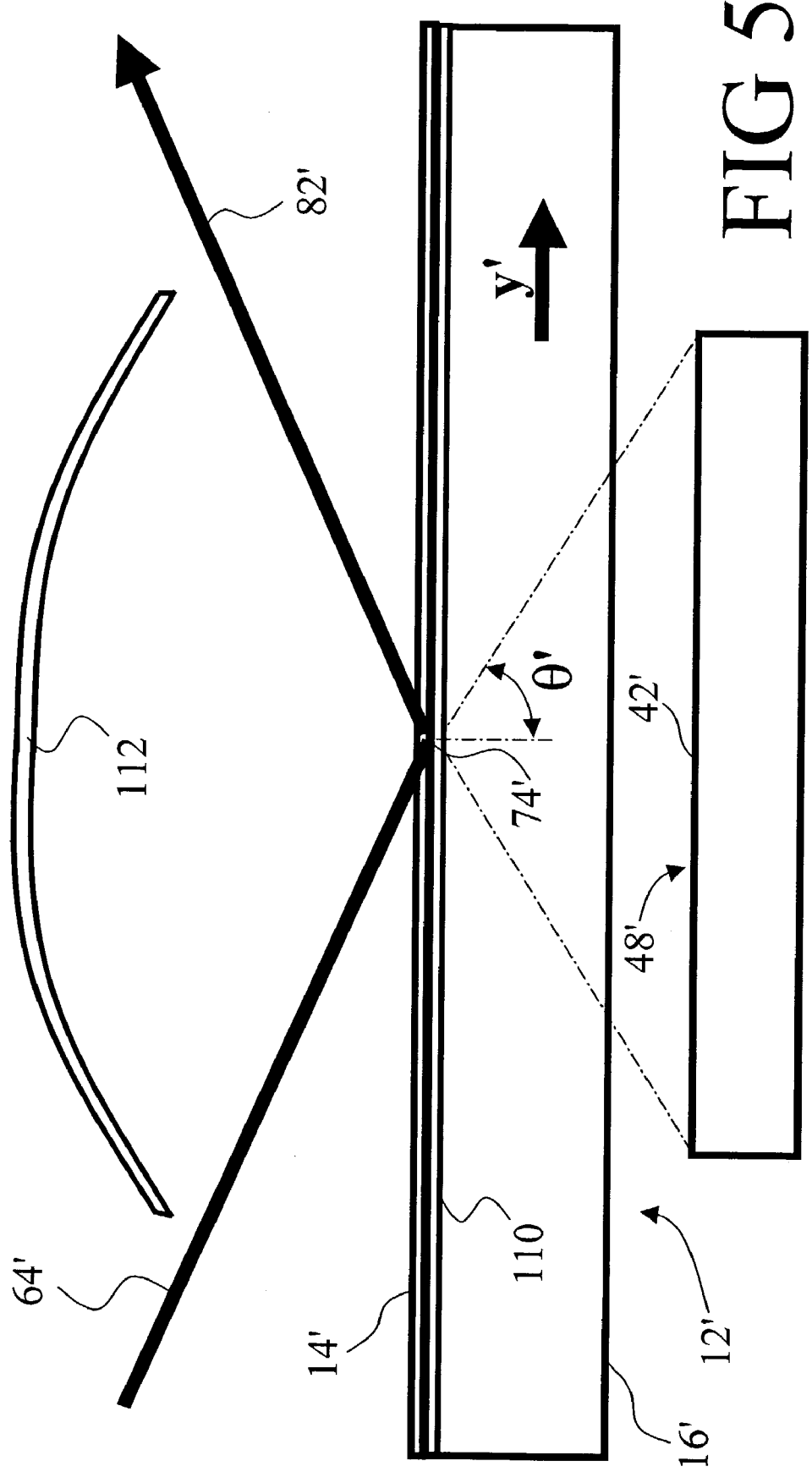
FIG. 5 shows a side view of another preferred embodiment of the invention, the view centered on the first end of the morphed fiber optic bundle.

With reference to FIG. 5, an alternative configuration of the scanning radiation source and the microscope aperture are described. In FIG. 5, elements which correspond to similar elements of the embodiment of FIGS. 1–4 are indicated by primed reference numbers, while new elements are indicated with unprimed reference numbers. In the embodiment of FIG. 5, a sample 12' includes a biological smear 14' coating a an imager slide 16' similarly to the sample 12. A radiation beam 64' impinges upon the sample 12' along a trajectory 74' perpendicular to a y'-direction in an orientation substantially similar to that shown in FIG. 4. An input aperture 48' is substantially similar to the input aperture 48 of FIGS. 1–4, and is defined by a first fiber bundle end 42'.

However, in the embodiment of FIG. 5 the input aperture 48' is arranged to view the sample 12' from below, i.e. from a side of the slide 16' that is opposite the biological smear 14'. That is, the input aperture 48' views the biological smear 14' through the slide 16', which is light-transmissive for the characteristic luminescence of the cells. The input aperture 48' has a short dimension along the y'-direction and a long dimension perpendicular to the y'-direction, and has a light collection angle θ'.

Because the slide 16' is substantially light-transmissive for the characteristic luminescence, characteristic luminescence directed toward the input aperture 48' and lying within the light collection window defined by the collection angle θ' passes through the slide 16' and is collected by the input aperture 48' and transmitted to an output aperture (not shown in FIG. 5) similarly to the embodiment of FIG. 1.

The slide 16' includes an optional laser blocking filter 110, such as an absorption band pass filter, coating the surface below the biological smear 14'. The laser blocking filter 110 reflects substantially all the radiation beam 64' to form a reflected beam 82'. Because the laser blocking filter 110 substantially prevents scattered components of the radiation beam from reaching the input aperture 48', an element corresponding to the laser-blocking filter 94 of the embodiment of FIG. 1 is optionally omitted in the embodiment of FIG. 5, i.e. is functionally replaced by the laser blocking filter 110. It will be appreciated that the laser blocking filter 110 can alternatively be disposed on an opposite side of the slide 16, i.e. on the side facing the input aperture 48'. In yet another contemplated variation, the slide 16' is light transmissive for the characteristic luminescence, but is substantially absorbing for the excitation radiation of the radiation beam 64', so that the slide 16' itself serves as the laser-blocking filter.

The embodiment of FIG. 5 also includes an optional cylindrical reflector 112 having a linear focal line generally coinciding with the radiation beam trajectory 74' on the biological smear 14'. The cylindrical reflector 112 reflects characteristic luminescence directed away from the input aperture 48' back through its generation point on the beam trajectory 74' and into the input aperture 48'. The cylindrical reflector 112 can improve the signal-to-noise ratio for certain imaging applications by increasing the amount of characteristic luminescence that is collected. It will be recognized that the cylindrical reflector 112 can also be used in conjunction with the configuration of FIGS. 1–4.

As discussed above, the imager of the present discussion may be implemented both in luminous and non-luminous applications. When designed for use in a non-luminous implementation, the blocking filter is not required. When used in luminous applications, the blocking filter is required, and that filter may be an absorptive filter located at the slide or substrate, may be the fiber bundle itself, or may be a filter located in the output optics section. Another filter which is noted to be used in luminous applications is a reflective or interference type filter, which may be coated on the slide or substrate, or located in the output optics.

With reference to FIG. 6, an alternative fiber optic bundle 40" is described, which is suitable for use in the apparatus embodiments of FIGS. 1–4 and FIG. 5. In FIG. 6, elements which correspond to similar elements of the optical fiber bundle 40 are indicated by double-primed reference numbers, i.e. a fiber optic bundle 40", while new elements are indicated with unprimed reference numbers. The optical fiber bundle 40" includes a plurality of first fiber ends 46" that collectively define a linear or high aspect ratio rectangular input aperture 48" that is similar to the input aperture 48. In FIG. 6, only a few fiber ends 46" are shown in schematic fashion. Preferably, the number of first fiber ends is in a range of thousands to tens of thousands or more. Each first fiber end 46" is a termination of a fiber, such as exemplary fibers 56", 58".

However, unlike the fiber optic bundle 40, the optical fibers 56", 58" of the fiber optic bundle 40" do not extend completely through to an output aperture 52". Instead, the optical fibers 56", 58" terminate at an optical coupler 120 which operates in known ways to combine light channeled by the plurality of fibers including the fibers 56", 58" into a single optical fiber or light pipe 122 which has a large diameter compared with the first fiber ends 46". The light pipe 122 has an end distal from the optical coupler 120 which defines the output aperture 52". Optionally, the distal end is narrowed, shaped to define a lensing surface, or otherwise modified (not shown in FIG. 6) to improve optical coupling with the output aperture 52". Although light pipe 122 is shown as straight in FIG. 6, it is to be appreciated that the light pipe 122 can be a rigid bent light pipe or a flexible light pipe. The optical fiber bundle 40" suitably substitutes for the optical fiber bundle 40 in FIGS. 1–4, or for the optical fiber bundle of the embodiment of FIG. 5.

Although the embodiments have been described with particular reference to cell identification, the invention is not limited in application thereto. The imager apparatus 10 of FIG. 1 is suitable for many imaging applications in which features are to be identified or located. In one such application lying in the biomedical arts, an array of typically ten to ten thousand DNA elements are arranged in an array known in the art as a DNA chip. The DNA elements are processed so that selected elements include a fluorescent tag. The apparatus of FIG. 1 is suitable for identifying the tagged DNA elements in a DNA chip that includes a large number of DNA elements. Implementing the concepts described in the foregoing permits for an imaging apparatus that can access the sample several times faster than existing technology.

Although the illustrated embodiments have been described with reference to detecting luminescence generated by tagged or treated cells, the imaging apparatus 10 is readily modified to detect other types of light signals. For example, the radiation beam 64 produced by the laser 62 typically produces scattered light as well as reflected light 82. The scattered light can be used for imaging by omitting the laser blocking filter 94 (or the laser blocking coating 110 in the embodiment of FIG. 5) so that the photodetector 98 is coupled to the output aperture to receive and detect the scattered laser light. The imaging apparatus 10 with laser blocking omitted is suitable for use in the electronics arts to identify non-specular defects on a polished semiconductor wafer. For epitaxial wafers with high quality epitaxial semiconductor films deposited thereon, or for wafers processed in a high-quality cleanroom environment, defects typically occur at low areal densities, and so are particularly suitable for characterization by the apparatus 10. Measured defect counts can be used for quality control screening in a wafer fabrication process.

Similarly, the imaging apparatus 10 is readily modified to image using the reflected beam 82. In addition to omitting the filter 94 (or film 110) as discussed in the previous paragraph, for this imaging mode the geometry shown in FIG. 4 is preferably adjusted so that the reflected beam 82 falls within the collection angle θ of the input aperture 48. To avoid having the input aperture 48 block the incident beam 64, the adjustment preferably includes tilting the input aperture 48 toward the reflected beam 82. That is, the input aperture 48 is positioned at a tilt relative to a surface normal of the imaged surface. The reflected beam imaging mode is suitable for counting or imaging low-density non-specular defects on polished surfaces of various types. The non-specular defects are imaged as decreases in the intensity of the reflected beam 82.

In yet another operating mode, the transmitted beam can be used for imaging. For example, the configuration of the embodiment of FIG. 5 can be modified by removing the laser blocking filter 110 and the cylindrical reflector 112 and tilting or translating the input aperture 48' to admit the transmitted portion of the radiation beam 64'. The radiation beam 64' is angularly adjusted to enter the input aperture 48'. For this imaging mode, a normal incidence of the radiation beam on the imaged surface can be suitable. An application of the transmission imaging mode is detection and counting of pinholes in opaque coatings, or recording light transmission differences in biological, organic, artificial or natural samples.

Figure 7A:
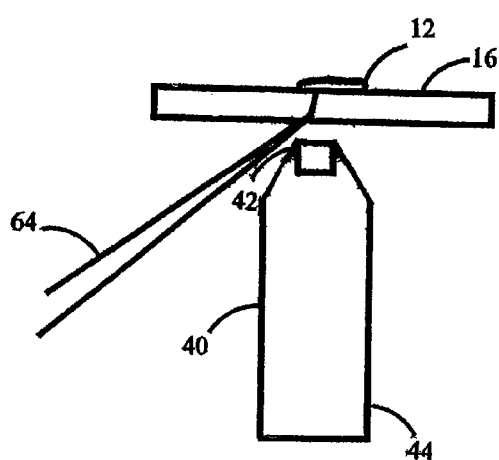
FIGS. 7A–7D reflect four permutations of the relationship between the fiber bundle head, the slide containing a sample, and the excitation beam path.

Turning to FIGS. 7A–7D, provided is a simplified illustration summarizing possible permutations for the relationship between the fiber optic bundle 40, radiation beam 64, slide 16 and sample 12. It is to be noted these permutations may be employed for each of the embodiments, applications and uses described in the foregoing discussion. With specific attention to FIG. 7A, the simplified fiber optic bundle 40, or other described fiber optic acquisition design, is shown positioned below slide 16 which is carrying on its front surface sample 12. First end 42 of bundle 40 is near slide 16. Further shown in FIG. 7A is radiation beam 64 projecting towards sample 12 from the underside of slide 16. In this embodiment the radiation beam is entering slide 16 at 60° to normal, although it is to be understood other angles are possible. Beam 64 is shown bending toward the normal inside slide 16 to reach sample 12. Such bending of the light being in accordance with Snell's Law.

Figure 7B:
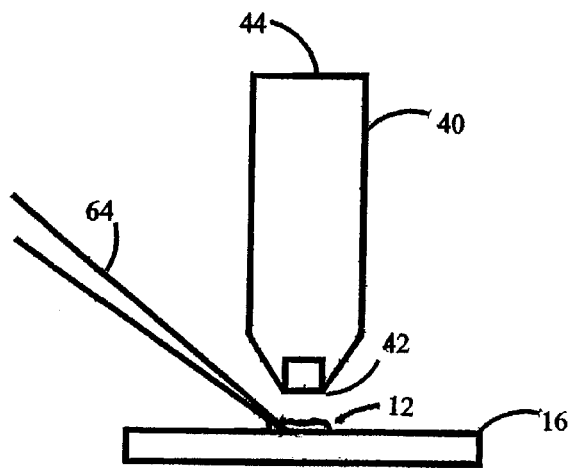

FIG. 7B represents an arrangement which has been described in reference to, for example, the previous figures such as FIG. 1. More specifically, the fiber optic bundle 40 having first end 42 closest to the sample 12 has radiation beam 64 interacting with sample 12 on the same side of slide 16. It is to be noted with regard to FIGS. 7A and 7B that the fiber optic bundle includes angled areas on the first end 42 such that the beam is not interfered with and the desired light collection is obtained. More specifically, as the excitation beam is projected to the slide and reflected off of the slide, interference is avoided via the angling of the first end 42.

Figure 7C:
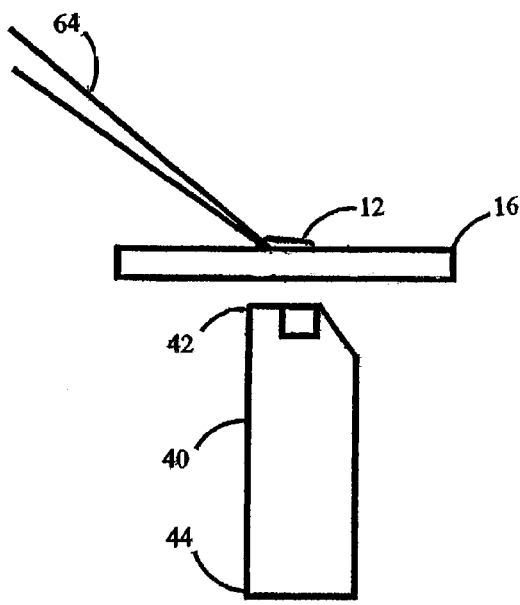

Turning to FIG. 7C, set forth is a permutation wherein the fiber optic bundle 40 is located beneath slide 16 and on the opposite side of sample 12. Radiation beam 64 is shown interacting with sample 12 on a front surface of slide 16, and has an angled side as in FIG. 7C. Further, fiber optic bundle 40 includes a single angled side to avoid undesirable reflectivity.

Figure 7D:
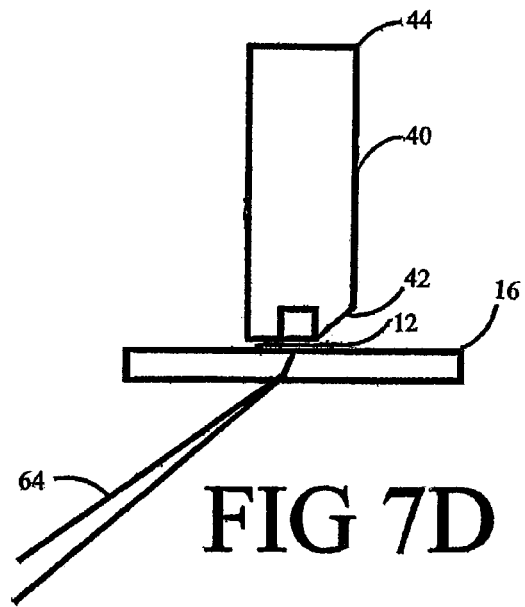

Lastly, FIG. 7D sets forth a permutation where the fiber optic bundle 40 is located on the same side as sample 12 carried on slide 16. The radiation beam 64 is shown interacting with sample 12 via a back side of the slide 16. By this design, the excitation beam 64 travels through slide 16, and therefore is again affected by Snell's Law.

Each of the permutations may be used dependant upon the application. These designs permit a varying of the amount of excitation beam which may be collected and/or how close the fiber optic bundle head may be located to the slide.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An imager for imaging a sample, the imager including:
   an imager stage that supports the sample;
   a fiber optic bundle having a proximate bundle end of first fiber ends arranged to define an input aperture viewing the sample on the imager stage, and a distal bundle end of second fiber ends arranged to define an output aperture shaped differently from the input aperture and disposed away from the imager stage;
   a scanning radiation source arranged in fixed relative position to the input aperture, the scanning radiation source scanning a radiation beam on the sample within a viewing area of the input aperture, the radiation beam interacting with the sample to produce a light signal that is received by the input aperture and transmitted via the fiber optic bundle to the output aperture;
   a photodetector arranged to detect the light signal at the distal bundle end; and
   a processor that processes the light signal detected by the photodetector.

2. The imager as set forth in claim 1, further including:
   a motor arranged to move the sample in one of a translational and a rotational motion, the motor cooperating with the scanning radiation source to effectuate a rastering of the radiation beam over a selected area of the sample.

3. The imager as set forth in claim 2, wherein the input aperture has a generally linear shape, the scanning radiation source scans the radiation beam along a beam trajectory parallel to the generally linear aperture, and the motor linearly translates the sample along a trajectory that is perpendicular to the beam trajectory.

4. The imager as set forth in claim 2, wherein the motor rotates the sample about an axis that is normal to a surface of the sample, the input aperture has a generally linear shape extending radially away from the rotational axis, and the scanning radiation source scans the radiation beam along a beam trajectory parallel to the generally linear aperture.

5. The imager as set forth in claim 1, including:
a photodetector coupled to the output aperture for detecting the emitted light signal.

6. The imager as set forth in claim 5, wherein the single photodetector is a photomultiplier tube.

7. The imager as set forth in claim 5, wherein the scanning radiation source is a light scanner, the imager further including:
a light filter arranged to substantially block light produced by the light scanner from reaching the photodetector.

8. The imager as set forth in claim 7, further including:
a substrate on which the sample is disposed, the substrate being supported by the translation stage, the light filter being arranged as a coating on the substrate.

9. The imager as set forth in claim 8, wherein the substrate is the light filter.

10. The imager as set forth in claim 7, wherein the fiber optic bundle is the light filter.

11. The imager as set forth in claim 7, wherein the light filter is located at the distal end of the fiber optic bundle.

12. The imager as set forth in claim 1, further including:
a lens for focusing the light signal from the output aperture onto a photodetector.

13. The imager as set forth in claim 1, wherein the light signal is a scattered, reflected, or transmitted portion of the radiation beam.

14. The imager as set forth in claim 1, wherein the light signal is a fluorescence generated by interaction of the radiation beam with the sample.

15. The imager as set forth in claim 1, wherein the input aperture is arranged with the first fiber ends substantially perpendicular to a surface of the sample, and the scanning radiation source is arranged to scan the radiation beam at an oblique angle respective to a normal axis of the surface of the sample, the oblique angle being outside a collection angle of the input aperture.

16. The imager as set forth in claim 1, wherein the input aperture has an area substantially comporting with a selected area of the sample, and the scanning radiation source rasters the radiation beam along two non-parallel directions to cover the selected area of the sample.

17. An imager for imaging a generally planar surface, the imager including:
a linearly translating stage that linearly translates the surface in a first direction;
a fiber optic bundle having a first end of parallel first fiber ends arranged to define a linear input aperture disposed perpendicular to the first direction and parallel to the surface, and a second end defining a generally circular output aperture, wherein each first fiber end optically communicates with the generally circular output aperture;
a scanning radiation source that linearly scans a radiation beam along the generally planar surface below the input aperture, the radiation beam interacting with the surface to produce a light signal that is collected by the input aperture and transmitted by the fiber optic bundle to the output aperture;
a photodetector arranged detect the light signal at the generally circular output aperture; and
a rastering processor communicating with the imager stage and the scanning radiation source to coordinate the scanning of the radiation beam and the linear translation of the surface to effectuate a rastering of the radiation beam on the surface.

18. The imager as set forth in claim 17, wherein the second end of the fiber optic bundle includes a plurality of parallel second fiber ends, each second fiber end connecting with a corresponding first fiber end by an optical fiber of the fiber optic bundle.

19. The imager as set forth in claim 17, wherein the fiber optic bundle further includes:
an optical coupler;
a plurality of optical fibers extending from the first fiber ends and optically combining at the optical coupler; and
a generally circular light pipe that communicates light from the optical coupler to the second end of the fiber optic bundle, wherein the generally circular output aperture corresponds with an end of the light pipe that is distal from the optical coupler.

20. The imager as set forth in claim 17, wherein the generally planar surface includes a slide surface coated with a biological fluid containing cells, the biological fluid being treated with a material that selectively couples with a selected cell type, the material producing the light signal responsive to interaction with the radiation beam.

21. An imaging method comprising:
sweeping a radiation beam along a linear path on a sample;
collecting light produced by beam interaction with the sample using at least one proximate element of an array of fiber optic ends formed in a generally linear shape;
transmitting the collected light along a fiber associated with the at least one proximate element, the fiber channeling the collected light to a selected output region formed in a generally circular shape, wherein a largest spatial dimension of the output region is substantially smaller than a largest spatial dimension of the array of fiber optic ends;
detecting the collected light at the selected output region;
moving the sample generally perpendicularly to the linear path of the radiation beam sweeping, the moving cooperating with the sweeping to raster of the radiation beam on the sample; and
coordinating the sweeping, moving, and detecting to generate an array of picture elements representative of at least a portion of the sample.

22. The imaging method as set forth in claim 21, further including:
filtering the collected light to remove radiation of the radiation beam therefrom.

23. The imaging method as set forth in claim 21, wherein the sample includes a biological smear, the imaging method further including:
marking the biological smear using a fluorescent material that selectively attaches to a selected type of cell, wherein the light produced by beam interaction includes fluorescence produced by the fluorescent material due to interaction with the radiation beam.

24. An apparatus for identifying cells in a biological smear, the cells emitting a characteristic luminescence responsive to exposure to an excitation radiation, the apparatus including:
a translating stage that laterally translates the biological smear in a first direction;
a fiber optic bundle including a plurality of fibers each having a first end and a second end, the first ends arranged to define a generally rectangular receiving aperture having a large aspect ratio, the second ends arranged to define an output aperture having a compact shape;
a radiation source that linearly sweeps an excitation radiation beam across the biological smear with a sweep direction perpendicular to the first direction, an interaction region of the radiation source and the biological smear being arranged relative to the receiving aperture such that characteristic luminescence produced in the interaction region is collected by the receiving aperture;

a photodetector arranged to detect the collected characteristic luminescence at the output aperture; and a controller that controls the translation of the translation stage and the sweeping of the radiation source to raster the excitation radiation beam across the biological smear to identify rare cells in the biological smear based upon the characteristic luminescence detected during the rastering.

25. The apparatus as set forth in claim 24, further including:

focusing optics that focus the collected characteristic luminescence at the output aperture onto the photodetector.

26. The apparatus as set forth in claim 24, further including:

filtering optics that selectively pass the characteristic luminescence.

27. The apparatus as set forth in claim 24, wherein a spot size of the excitation radiation beam on the biological smear substantially comports with a size of the cells.

28. The apparatus as set forth in claim 24, wherein a spot size of the excitation radiation beam on the biological smear is adjusted to be substantially the cell size.

29. The apparatus as set forth in claim 24, wherein the output aperture is generally circular.

30. The apparatus as set forth in claim 24, further including:

a reflector arranged to reflect characteristic luminescence produced in the interaction region and directed away from the receiving aperture back toward the receiving aperture.

31. The apparatus as set forth in claim 24, further including:

a counter that counts a number of cells based upon characteristic luminescence detected during the rastering.

32. The apparatus as set forth in claim 24, further including:

an image processor that computes an image representation including spatial positions of cells in the biological smear based upon characteristic luminescence detected during the rastering and corresponding coordinates of the translating stage and the sweeping excitation radiation beam; and a display device that displays the image representation in a human-viewable format.

33. An imaging apparatus for imaging a sample, the imaging apparatus including:

an imager stage supporting a slide on which the sample is disposed, the slide including a wavelength-selective filter disposed thereon which substantially blocks light at an excitation light wavelength;

a radiation source including a light source that emits excitation light at the excitation light wavelength, and optics that convert the emitted excitation light into collimated excitation light that impinges on the sample, wherein interaction between the excitation light and the sample generates luminescence light at a different wavelength from the excitation light wavelength;

an input aperture arranged to collect at least a portion of the luminescence light, the input aperture arranged on an opposite side of the slide from the impinging excitation light such that the wavelength-selective filter substantially blocks excitation light from being collected by the input aperture; and an output aperture optically communicating with the input aperture and emitting the luminescence light collected by the input aperture.

34. An imager for imaging a sample, the imager including:

an imager stage that supports the sample;

a light transmission mechanism having a generally linear shaped input aperture disposed proximate the sample on the imager stage, and a generally circular shaped output aperture disposed distant from the imager stage, the input aperture and output aperture connected via an enclosed light path;

a scanning radiation source arranged in fixed relative position to the input aperture, the scanning radiation source scanning a radiation beam on the sample within a viewing area of the input aperture, the radiation beam interacting with the sample to produce a light signal that is received by the input aperture and transmitted via the enclosed light path to the output aperture;

a detector arrangement positioned to detect the light signal at the output aperture; and a processor that processes the light signal detected by the detector.

* * * * *